United States Patent
Azar

(10) Patent No.: US 9,254,189 B2
(45) Date of Patent: Feb. 9, 2016

(54) ABERRATION-CORRECTING VISION PROSTHESIS

(75) Inventor: Dimitri T. Azar, Chicago, IL (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 79 days.

(21) Appl. No.: 13/413,504

(22) Filed: Mar. 6, 2012

(65) Prior Publication Data

US 2012/0239144 A1    Sep. 20, 2012

Related U.S. Application Data

(60) Continuation of application No. 12/542,143, filed on Aug. 17, 2009, now abandoned, which is a division of application No. 10/712,294, filed on Nov. 13, 2003, now abandoned.

(51) Int. Cl.
*A61F 2/16*    (2006.01)

(52) U.S. Cl.
CPC .............. *A61F 2/1637* (2013.01); *A61F 2/16* (2013.01); *A61F 2/1627* (2013.01); *A61F 2/1635* (2013.01)

(58) Field of Classification Search
CPC .............. A61F 2/1618; A61F 2/1629; A61F 2002/164; A61F 2/16; A61F 2/1613; A61F 2/1624–2/1637

USPC ................................ 623/4.1, 6.22–6.24, 6.33
See application file for complete search history.

(56) References Cited

U.S. PATENT DOCUMENTS

| | | | |
|---|---|---|---|
| 4,190,330 A | 2/1980 | Berreman |
| 4,230,942 A | 10/1980 | Stauffer |
| 4,309,603 A | 1/1982 | Stauffer |
| 4,373,218 A | 2/1983 | Schachar |
| 4,466,703 A | 8/1984 | Nishimoto |
| 4,601,545 A | 7/1986 | Kern |
| 4,787,903 A | 11/1988 | Grendahl |
| 5,108,429 A | 4/1992 | Wiley |
| 5,182,585 A | 1/1993 | Stoner |
| 5,359,444 A | 10/1994 | Piosenka et al. |
| 5,593,437 A | 1/1997 | Arita et al. |
| 5,800,530 A | 9/1998 | Rizzo, III |
| 6,413,276 B1 | 7/2002 | Werblin |
| 6,638,304 B2 | 10/2003 | Azar |
| 6,749,632 B2 | 6/2004 | Sandstedt et al. |
| 7,127,299 B2 | 10/2006 | Nelson et al. |
| 2002/0016629 A1 | 2/2002 | Sandstedt et al. |
| 2004/0156014 A1 | 8/2004 | Piers et al. |

*Primary Examiner* — Howie Matthews
(74) *Attorney, Agent, or Firm* — Fish & Richardson P.C.

(57) ABSTRACT

A vision prosthesis includes an optical element having a characteristic function associated with refraction therethrough. The characteristic function is selected to reduce aberration in an eye when the optical element is implanted at a location therein.

20 Claims, 4 Drawing Sheets

ABERRATION-CORRECTING VISION PROSTHESIS

CROSS-REFERENCE TO RELATED APPLICATIONS

This application is a continuation application of and claims priority to U.S. application Ser. No. 12/542,143, filed on Aug. 17, 2009, which is a divisional application and claims priority to U.S. application Ser. No. 10/712,294, filed on Nov. 13, 2003, the entire contents of which are incorporated herein by reference.

FIELD OF INVENTION

The invention relates to an aberration correcting vision prosthesis.

BACKGROUND

In the course of daily life, one typically regards objects located at different distances from the eye. To selectively focus on such objects, the focal length of the eye's lens must change. In a healthy eye, this is achieved through the contraction of a ciliary muscle that is mechanically coupled to the lens. To the extent that the ciliary muscle contracts, it deforms the lens. This deformation changes the focal length of the lens. By selectively deforming the lens in this manner, it becomes possible to focus on objects that are at different distances from the eye. This process of selectively focusing on objects at different distances is referred to as "accommodation."

As a person ages, the lens loses plasticity. As a result, it becomes increasingly difficult to deform the lens sufficiently to focus on objects at different distances. This condition is known as presbyopia. Refractive errors caused by such conditions as hyperopia, myopia, as well as aberrations due to irregularities in the eye (e.g., in the cornea or in the natural crystalline lens) can also cause problems in one's ability to focus on an object. To compensate for this loss of function, it is useful to provide different optical corrections for focusing on objects at different distances. Some restoration of focusing ability for some distances can be provided by spectacles or contact lenses.

There are also a variety of disorders that degrade the ability of the eye to function properly. These include vitreoretinal disorders, lenticular disorders, corneal disorders, and glaucomatous states. Some treatments to some of these types of disorders involve surgical intervention. For example, a common disorder involves progressive clouding of the natural crystalline lens resulting in the formation of what is referred to as a cataract. A common practice used to treat a cataract is surgically removing the cataractous natural crystalline lens and implanting (in the "aphakic" patient) an artificial intraocular lens into the empty lens bag to replace the natural crystalline lens. After cataract surgery, the corneal incision (and/or limbal and scleral incisions) can potentially induce optical aberrations due to altered corneal curvature and topography. Intraocular lenses can also be used for a "phakic" patient who still has a natural crystalline lens.

SUMMARY

In one aspect, the invention features a vision prosthesis including an optical element having a characteristic function associated with refraction therethrough. The characteristic function is selected to reduce aberration in an eye when the optical element is implanted at a location therein.

In one embodiment the vision prosthesis includes a modifiable part for selectively modifying the characteristic function of the optical element.

The modifiable part can include a wavefront component that is releasably attachable to the optical element, and the wavefront component has a surface shaped to reduce the aberration in the eye. The shape of the surface is formed using wavefront-guided laser ablation. The wavefront component and the optical element have relative orientation features.

Alternatively, the modifiable part can include a memory element in the vision prosthesis. The memory element stores modifiable wavefront data selected to control an index of refraction profile of the optical element to reduce the aberration in the eye.

Alternatively, the modifiable part can include a deformable material whose shape is configured to change in response to an actuator.

In another embodiment, the vision prosthesis includes a range-finder for generating, from a stimulus, an estimate of a distance to an object-of-regard. An actuator in communication with the optical element provides a signal that controls the focusing power of the optical element. A controller is coupled to the rangefinder and to the actuator, for causing the actuator to generate the signal based on the estimate.

In another embodiment, the vision prosthesis includes an actuator in communication with the optical element for providing a signal that controls the characteristic function of the optical element. A controller is coupled to the actuator for causing the actuator to generate the signal based on wavefront data stored in a memory element of the controller.

The signal can be a parallel signal carried over a plurality of signal lines addressing a corresponding plurality of electrodes on the actuator. The characteristic function of the optical element changes in response to the signal by changing an index of refraction of material within the optical element at a plurality of locations.

Alternatively, the characteristic function of the optical element changes in response to the signal by changing shape of a surface of the optical element.

In some embodiments, the vision prosthesis includes a rangefinder coupled to the controller for generating, from a stimulus, an estimate of a distance to an object-of-regard. The signal is based on the estimate, and the focusing power and/or characteristic function of the optical element changes in response to the estimate.

When implanted in the eye, the optical element can be disposed at a variety of locations, such as the anterior chamber, the posterior chamber, the lens-bag, and the cornea.

The vision prosthesis can be adapted for implantation in a phakic human patient, or for implantation in an aphakic human patient.

In another aspect, the invention features a method including implanting an optical element into an eye, measuring aberration in the eye when the optical element is implanted in the eye, determining wavefront data based on the measured aberration, and programming the wavefront data into a memory device in electrical communication with the optical element. A characteristic function associated with refraction through the optical element is designed to reduce aberration in the eye after the memory device is programmed.

In another aspect, the invention features a method including implanting an optical element into an eye, measuring aberration in the eye when the optical element is implanted in the eye, shaping a wavefront component based on the measured aberration, inserting the wavefront component into the eye, and attaching the wavefront component to the optical element. A characteristic function associated with refraction through the optical element is designed to reduce aberration in the eye after the wavefront component is attached.

As used herein, "aberration" means any one or combination of low-order or high-order aberration (including spherical aberration, coma, astigmatism, field curvature, and distortion), or chromatic aberration.

As used herein, a "characteristic function" means a function such as a point characteristic, an angle characteristic, or a mixed characteristic that describes refraction of a wavefront of light through a medium.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will become apparent from the following description, and from the claims.

DESCRIPTION

Figure 1:
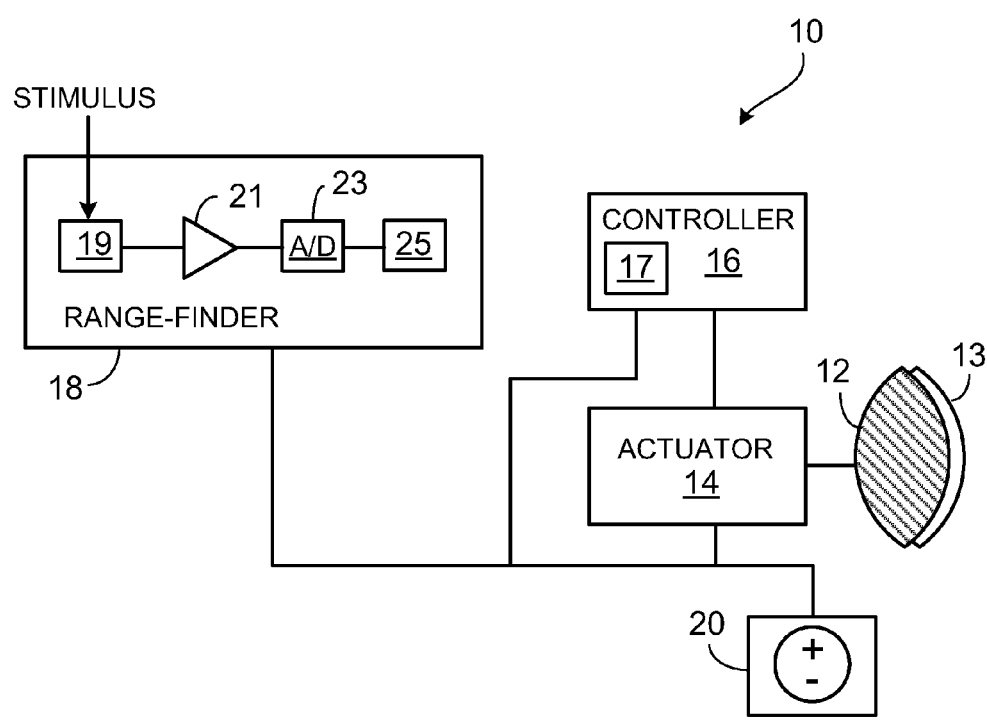
FIG. 1 is a block diagram of a vision prosthesis.

FIG. 1 shows a block diagram of a vision prosthesis 10 having an optical element 12 whose focusing power can be made to vary in response to a signal provided to the optical element 12 by an actuator 14. Techniques for changing the focusing power of the optical element 12 include changing the shape and/or index of refraction of material within the optical element. In one implementation, the optical element 12 includes a nematic liquid-crystal whose index of refraction varies in response to an applied electric field, and the actuator 14 includes one or more electrodes in electrical communication with the optical element 12. Alternatively, the optical element 12 collects light through a material whose index of refraction varies in response to an applied magnetic field. In this case, the actuator 14 is a magnetic field source, such as a current-carrying coil, in magnetic communication with the optical element 12. In addition, to or instead of, a change in index of refraction, the shape of a movable surface of the optical element 12 changes (e.g., chemically or mechanically) in response to the signal provided by the actuator 14. In another embodiment, the optical element includes a movable component for focusing. In this case, the actuator 14 moves one or more lenses or lens components along the visual axis to change the focal length of the optical element 12.

The vision prosthesis 10 provides accommodative adjustments and corrects for wavefront aberrations present in a patient's eye (e.g., due to abnormalities in the cornea, the natural crystalline lens, or the ocular media). The nature of the signal provided by the actuator 14 controls the extent to which a shape and/or index of refraction of the optical element 12 is changed and the corresponding level of accommodation. The actuator 14 generates a signal in response to instructions from a controller 16 in communication with the actuator 14. Corrections for wavefront aberrations in the eye can be made based on wavefront data stored in a memory device 17 in the controller 16. Alternatively, wavefront corrections can be made using a wavefront component 13 attached to the optical element 12. Either of these techniques can be used, alone or in combination. Both techniques are described in more detail below.

The controller 16 is typically a microcontroller having instructions encoded therein. These instructions can be implemented as software or firmware. However, the instructions can also be encoded directly in hardware in, for example, an application-specific integrated circuit. The instructions provided to the microcontroller include instructions for receiving, from a range-finder 18, data indicative of the distance-of-regard (i.e., distance to an object-of-regard), and instructions for processing that data to obtain a signal for focusing, and optionally, for wavefront aberration correction. The actuator 14 uses the signal to alter the optical element's properties to focus an aberration-corrected image of the object-of-regard on the retina.

The rangefinder 18 typically includes a transducer 19 for detecting a stimulus from which a range to an object can be inferred. The signal generated by the transducer 19 often requires amplification before it is of sufficient power to provide to the controller 16. Additionally, the signal may require some preliminary signal conditioning. Accordingly, in addition to a transducer 19, the rangefinder 18 includes an amplifier 21 to amplify the signal, an A/D converter 23 to sample the resultant amplified signal, and a digital signal processor 25 to receive the sampled signal. The digital signal processor 25 optionally performs signal conditioning (e.g., noise reduction or pattern matching). The output of the digital signal processor 25 is provided to the controller 16.

A power source 20 supplies power to the controller 16, the range finder 18, and the actuator 14. A single power source 20 can provide power to all three components. However, the vision prosthesis 10 can also include a separate power source 20 for any combination of those components that require power.

Wavefront Correction

To correct for wavefront aberrations, the change in shape, or index of refraction, of the optical element 12 is made a function of more than one spatial variable. By providing a plurality of actuating elements coupled to different local regions of the optical element 12 (e.g., distributed in a polar grid or a rectilinear grid), the optical path length through the optical element 12 can be varied at those local regions. For example, electrodes can apply a field to change the local refractive index, or mechanical actuators can apply force to deform local regions of a reflecting or refracting surface. An artificial muscle system (e.g., based on contractile polymers) can be used to change the shape of an optical element 12 to reduce wavefront aberrations.

A wavefront of light passing through the optical element 12 will be altered in a way that can be described by a characteristic function associated with refraction through the optical element 12. The characteristic function of an optical element can be estimated from knowledge of the optical path length traversed by any ray of light passing through any portion of the element. For an optical element comprised of various media having various surfaces, the optical path length can be determined from the index of refraction within the various media and the shapes of its surfaces. This type of analysis can also be used to design and construct an optical element having a desired characteristic function.

By measuring any pre-existing aberrations in a patient's eye, the optical element 12 can be designed to have a characteristic function that counters the effects of pre-existing aberrations. As a result, an optical element 12 implanted at a location intersecting the eye's visual axis reduces any remaining aberrations compared to the pre-existing aberrations. The optical element 12 can be located at any of a variety of locations including in front of the iris 26, sutured to the iris 26, hooked to the iris 26, sutured to the sulcus, or in the lens-bag 22.

Programmable Wavefront Correction

Figure 2:
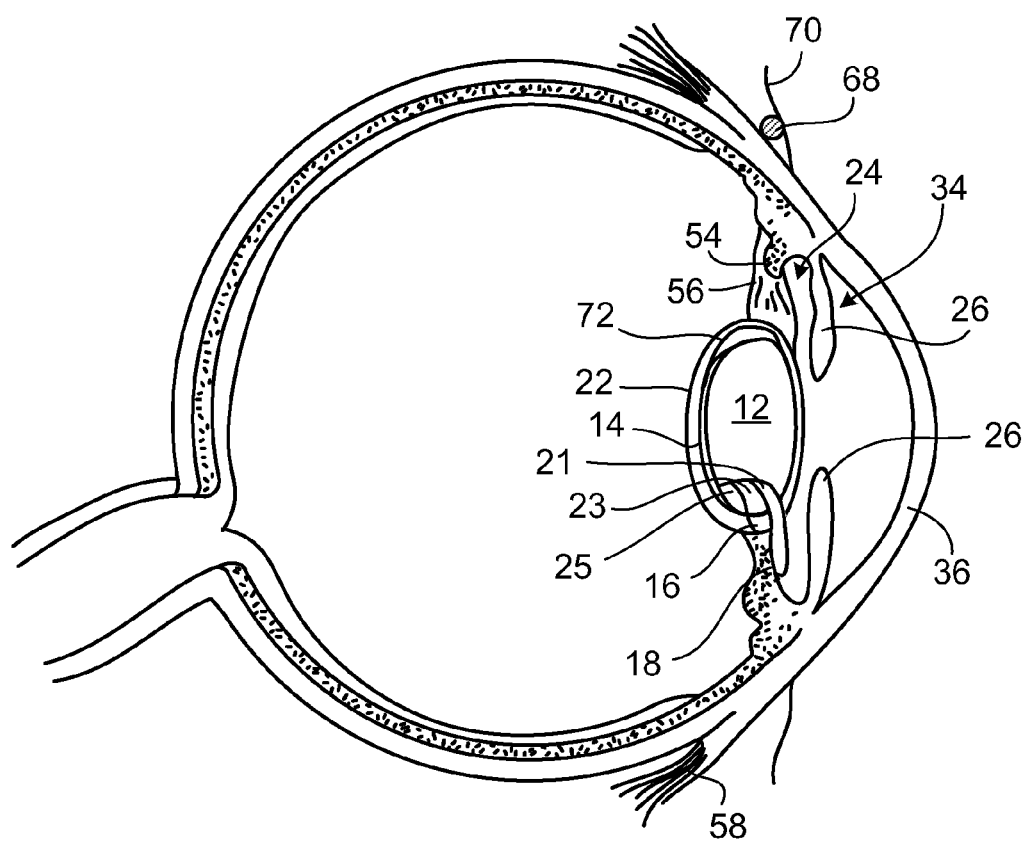
FIG. 2 shows an embodiment of the vision prosthesis of FIG. 1 using a controller to provide wavefront correction.

Referring to FIG. 2, in one embodiment of the vision prosthesis 10, the optical the optical element 12 is implanted into the lens-bag 22 of an aphakic patient. For a phakic patient, the optical element 12 is implanted behind the iris 26 in the posterior chamber 24, in front of the iris 26 in the anterior chamber 34, or in the cornea 36. As described in connection with FIG. 1, a transducer 19 transfers an electrical or mechanical stimulus from the eye through an amplifier 21, an A/D converter 23, and a digital signal processor 25, to a controller 16, all of which are located at the periphery of the optical element 12. A range-finder 18 can include one or more transducers 19 that sense stimuli from any of a variety of locations, such as the ciliary muscle 54, the zonules 56, or the lens-bag 22, as described in more detail below. A power source 20 can include a battery 68 under the conjunctiva 70 and/or a photovoltaic cell 72 at the periphery of the optical element 12 (e.g., in an annulus), also described in more detail below.

The controller 16 includes wavefront data (stored in a memory device 17) based on a wavefront aberration measurement performed on a patient. The optical element 12 includes an artificial intraocular lens that changes its shape and/or index of refraction over a two-dimensional surface or grid in response to a signal from the actuator 14. The controller 16 uses the wavefront data to determine point-by-point (over the two-dimensional surface or grid) the signal provided by the actuator 14 in response to the output of the range-finder 18.

To measure wavefront aberrations in a patient's eye, a surgeon measures anatomical features of the eye. For a patient undergoing cataract surgery (i.e., removal of part or all of the natural crystalline lens), it is useful to obtain measurements that do not change after the cataract surgery. For example, valid measurements can be obtained from axial lengths of structures of the eye (including the depth of the anterior chamber 34), corneal topography, and influence of certain incisions (e.g., corneal, scleral, or corneoscleral) on corneal topography.

These measurements are used to predict wavefront aberrations in the eye after cataract surgery. An ideal shape and/or index of refraction across the light collecting portion of the optical element 12, that corrects the predicted wavefront aberrations, is obtained by generating wavefront data based on the predicted wavefront aberrations.

The resulting wavefront corrections may be different for different distances-of-regard. The wavefront data should therefore depend on distance of regard. One way to accomplish this is by performing separate measurements of the anatomical features of the eye while the patient is focusing on objects at different distances. Another way to obtain wavefront data that depend on distance-of-regard is to incorporate the dependence into the wavefront data based on theoretical calculations of predicted changes to optical path lengths in the eye that occur during accommodation (e.g., changes to the natural crystalline lens for a phakic patient or changes to an artificial intraocular lens in an aphakic patient). The controller 16 can then use the wavefront data to cause the actuator 14 to provide different signals for different range estimates provided by the range-finder 18, thereby correcting wavefront aberration in a manner that depends in part on what the patient is looking at.

The wavefront data are also calculated based on predetermined position and orientation for the optical element within the patient's eye. After preparing components of the vision prosthesis, the surgeon implants the prosthesis as close as possible to the predetermined position and orientation within the patient's eye. If a patient is also undergoing cataract surgery and wavefront data in the controller 16 are based on measurements before the patient's natural crystalline lens has been removed, adjustments can be made based on measurements of postoperative deviations due to removal of the natural crystalline lens. Adjustments can also be made based on postoperative deviations in the position or orientation of the optical element 12 from the predetermined position and orientation. The wavefront data can also be updated based on changes that occur in the patient's vision (e.g., due to healing after surgery or aging).

Such adjustments can be performed, for example, by removing the controller 16, re-programming it with new wavefront data, and replacing it. Alternatively, the controller 16 can be re-programmed in situ by transmitting data over an encrypted wireless link (e.g., an infrared beam). The controller 16 uses encryption to ensure that only an authorized user (e.g., a surgeon) can gain access to the wavefront data (e.g., for updating or testing).

Ablated Surface Wavefront Correction

Figure 3:
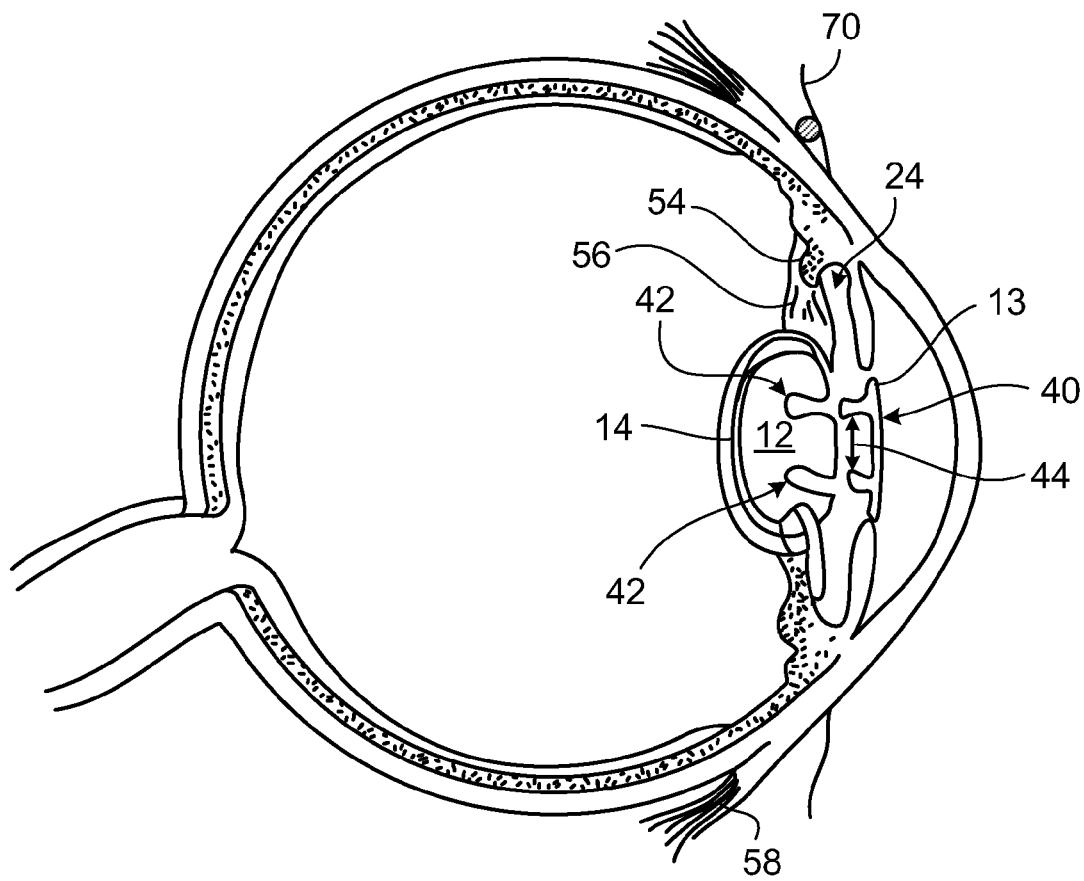
FIG. 3 shows another embodiment of the vision prosthesis of FIG. 1 using a wavefront component to provide wavefront correction.

In another embodiment, shown in FIG. 3, the wavefront correction is implemented by a releasably attachable wavefront component 13. In this embodiment, the optical element 12 is placed in a patient's eye (along with an actuator 14, controller 16, and range-finder 18) in a first surgical procedure. After the first surgical procedure, measurements of wavefront aberrations of the postoperative eye are taken. These measurements are used to perform wavefront-guided laser ablation on a surface 40 of a wavefront component 13. In a second surgical procedure, the wavefront component 13 is mated with the optical element 12 at a predetermined location. The wavefront component 13 is designed for a particular distance-of-regard (e.g., an average or preferred distance). However, the wavefront component 13 can be easily replaced with another wavefront component designed for a different distance-of-regard.

In the second surgical procedure, the wavefront component 13 is folded and inserted through a small incision, maneuvered into the desired location, and released. Once released, the component 13 springs back to its unfolded position. Since the second surgical procedure is less invasive than the first surgical procedure, it is less likely to induce further aberrations than the first surgical procedure.

The optical element 12 mates with the wavefront component 13 in such a way that the wavefront component 13 is in a predetermined position and orientation relative to the optical element 12. The optical element 12 and the wavefront component 13 have relative orientation features, such as at least two asymmetrically placed positioning holes 42 on the optical element and corresponding tabs 44 on the wavefront component 13. A specialized surgical tool can be used to facilitate engagement or replacement of the wavefront component 13. Alternative techniques for mating the wavefront component 13 to the optical element 12 include spinning the wavefront component 13 into a specialized groove, unfolding the wavefront component 13 into raised hooks, or connecting the wavefront component 13 to another component, such as a transducer 19.

The ablated surface 40 of the wavefront component 13 is shaped to correct for the wavefront aberrations present in the eye after the first surgical procedure. Laser ablation can be performed using an excimer laser on a wavefront component 13 composed of a material such as polymethyl methacrylate (PMMA) or acrylic. Alternatively, the wavefront component 13 can be etched to the desired shape using mechanical or photochemical etching. The resulting surface 40 of the wavefront component 13 is shaped to correct for wavefront aberrations when positioned in the eye, taking into account the difference between the index of refraction of the material of the wavefront component 13 and the index of refraction of the aqueous humor inside the eye.

Figure 4:
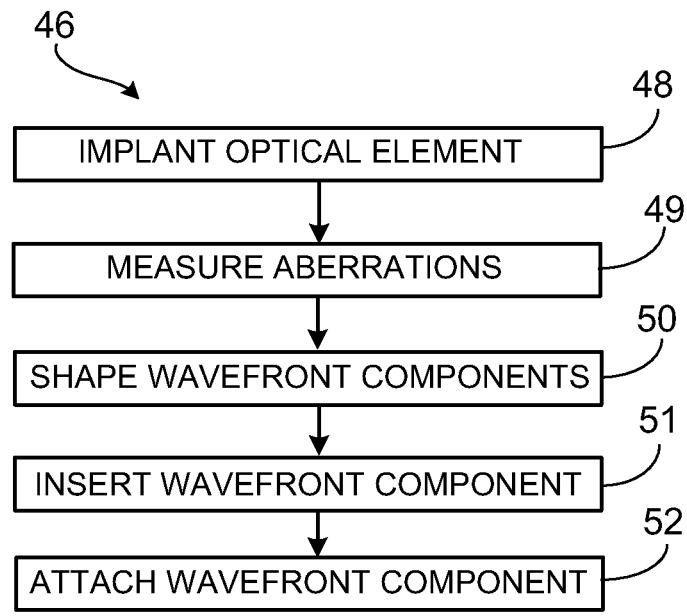
FIG. 4 is a procedure for preparing and implanting the vision prosthesis of FIG. 3.

Referring to FIG. 4, an exemplary procedure 46 for implanting the vision prosthesis shown in FIG. 3 includes implanting 48 the optical element 12 into the eye in the first surgical procedure. After the optical element 12 is implanted, the procedure 46 includes measuring 49 any aberration in the eye, including any effects of the optical element 12. Based on the measured aberrations, laser-ablation is used to shape 50 a surface of the wavefront component 13 to reduce aberration in the eye after the wavefront component 13 is installed. The wavefront component 13 is installed by inserting 51 the folded wavefront component 13 into a small incision in the eye and attaching 52 the unfolded wavefront component 13 to the optical element 12.

Rangefinder

In a normal eye, contraction of a ciliary muscle 54 is transmitted to the natural crystalline lens by zonules 56 extending between the ciliary muscle 54 and the lens-bag 22. When an object-of-regard is nearby, the ciliary muscle 54 contracts, thereby deforming the natural crystalline lens so as to bring an image of the object into focus on the retina. When the object-of-regard is distant, the ciliary muscle 54 relaxes, thereby restoring the natural crystalline lens to a shape that brings distant objects into focus on the retina. The activity of the ciliary muscle 54 thus provides an indication of the range to an object-of-regard.

The transducer 19 of the rangefinder 18 can be a transducer for detecting contraction of the ciliary muscle 54. In one implementation, the rangefinder 18 can include a pressure transducer that detects the mechanical activity of the ciliary muscle 54. A pressure transducer coupled to the ciliary muscle 54 can be a piezoelectric device that deforms, and hence generates a voltage, in response to contraction of the ciliary muscle 54. In another implementation, the transducer 19 can include an electromyograph for detecting electrical activity within the ciliary muscle 54.

As noted above, the activity of the ciliary muscle 54 is transmitted to the natural crystalline lens by zonules 56 extending between the ciliary muscle 54 and the lens-bag 22. Both the tension in the zonules 56 and the resulting mechanical disturbance of the lens-bag 22 can be also used as indicators of the distance to the object-of-regard. In recognition of this, the rangefinder 18 can also include a tension measuring transducer in communication with the zonules 56 or a motion sensing transducer in communication with the lens-bag 22. These sensors can likewise be piezoelectric devices that generate a voltage in response to mechanical stimuli.

The activity of the rectus muscles 58 can also be used to infer the distance to an object-of-regard. For example, a contraction of the rectus muscles 58 that would cause the eye to converge medially can suggest that the object-of-regard is nearby, whereas contraction of the rectus muscles 58 that would cause the eye to gaze forward might suggest that the object-of-regard is distant. The rangefinder 18 can thus include a transducer 19 that responds to either mechanical motion of the rectus muscles 58 or to the electrical activity that triggers that mechanical motion.

It is also known that when a person intends to focus on a nearby object, the iris 26 contracts the pupil 60. Another embodiment of the rangefinder 18 relies on this contraction to provide information indicative of the distance to the object-of-regard. In this embodiment, the rangefinder 18 includes a transducer 19, similar to that described above in connection with the rangefinder 18 that uses ciliary muscle or rectus muscle activity, to estimate the distance to the object-of-regard. Additionally, since contraction of the pupil 60 diminishes the light incident on the optical element 12, the transducer 19 of the rangefinder 18 can include a photodetector for detecting this change in the light.

The foregoing embodiments of the rangefinder 18 are intended to be implanted into a patient, where they can be coupled to the anatomical structures of the eye. This configuration, in which the dynamic properties of one or more anatomical structures of the eye are used to infer the distance to an object-of-regard, is advantageous because those properties are under the patient's control. As a result, the patient can, to a certain extent, provide feedback to the rangefinder 18 by controlling those dynamic properties. For example, where the rangefinder 18 includes a transducer responsive to the ciliary muscle 54, the patient can control the index of refraction of the optical element 12 by appropriately contracting or relaxing the ciliary muscle 54.

Other embodiments of the rangefinder 18 can provide an estimate of the range without relying on stimuli from anatomic structures of the eye. For example, a rangefinder 18 similar to that used in an auto-focus camera can be implanted. An example of such a rangefinder 18 is one that transmits a beam of infrared radiation, detects a reflected beam, and estimates range on the basis of that reflected beam. The output of the rangefinder 18 can then be communicated to the actuator 14. Since a rangefinder 18 of this type does not rely on stimuli from anatomic structures of the eye, it need not be implanted in the eye at all. Instead, it can be worn on an eyeglass frame or even hand-held and pointed at objects of regard. In such a case, the signal from the rangefinder 18 can be communicated to the actuator 14 either by a wire connected to an implanted actuator 14 or by a wireless link.

A rangefinder 18 that does not rely on stimuli from an anatomic structure within the eye no longer enjoys feedback from the patient. As a result, it is desirable to provide a feedback mechanism to enhance the range-finder's ability to achieve and maintain focus on an object-of-regard.

Figure 5:
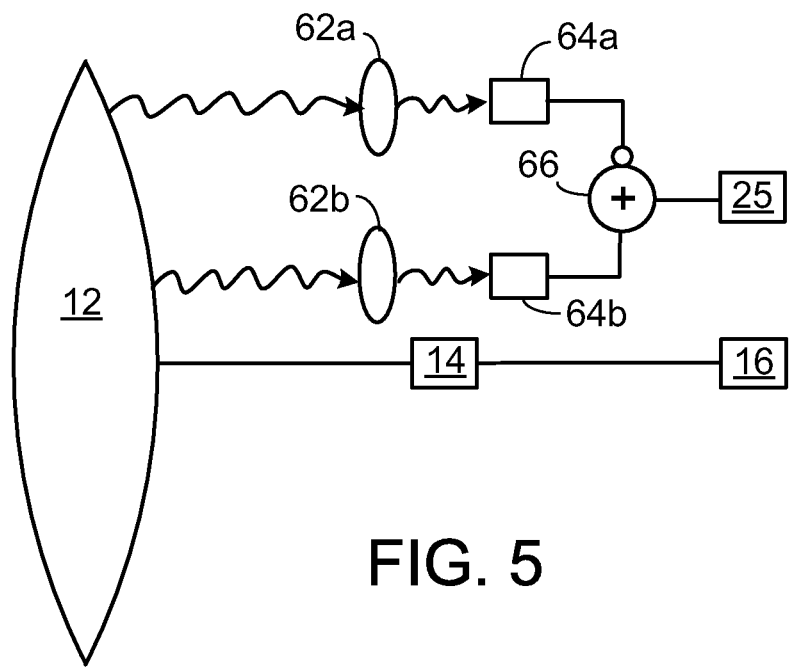
FIG. 5 shows a feedback mechanism for a rangefinder of the vision prosthesis of FIG. 1.

In a feedback mechanism as shown in FIG. 5, first and second lenslets 62a, 62b are disposed posterior to the optical element 12. The first and second lenslets 62a, 62b are preferably disposed near the periphery of the optical element 12 to avoid interfering with the patient's vision. A first photodetector 64a is disposed at a selected distance posterior to the first lenslet 62a, and a second photodetector 64b is disposed at the same selected distance posterior to the second lenslet 62b. The focal length of the first lenslet 62a is slightly greater than the selected distance, whereas the focal length of the second lenslet 62b is slightly less than the selected distance.

The outputs of the first and second photodetectors 64a, 64b are connected to a differencing element 66 that evaluates the difference between their output. This difference is provided to the digital signal processor 25. When the output of the differencing element 66 is zero, the optical element 12 is in focus. When the output of the differencing element 66 is non-zero, the sign of the output identifies whether the focal length of the optical element 12 needs to be increased or decreased, and the magnitude of the output determines the extent to which the focal length of the optical element 12 needs to change to bring the optical element 12 into focus. A feedback mechanism of this type is disclosed in U.S. Pat. No. 4,309,603, the contents of which are herein incorporated by reference.

In any of the above embodiments of the rangefinder 18, a manual control can also be provided to enable a patient to fine-tune the focusing signal. The digital signal processor 25 can then use any correction provided by the user to calibrate the range estimates provided by the rangefinder 18 so that the next time that that range estimate is received, the focusing signal provided by the digital signal processor 25 will no longer need fine-tuning by the patient. This results in a self-calibrating vision prosthesis 10.

The choice of which of the above range-finders is to be used depends on the particular application. For example, an optical element 12 implanted in the posterior chamber 24 has ready access to the ciliary muscle 54 near the transducer 19. Under these circumstances, a rangefinder that detects ciliary muscle activity is a suitable choice. An optical element 12 implanted in the anterior chamber 34 is conveniently located relative to the iris 26 but cannot easily be coupled to the ciliary muscle 54. Hence, under these circumstances, a rangefinder that detects contraction of the iris 26 is a suitable choice. An optical element 12 implanted in the cornea 36 is conveniently located relative to the rectus muscles 58. Hence, under these circumstances, a rangefinder that detects contraction of the rectus muscles 58 is a suitable choice. In the case of an aphakic patient, in which the natural crystalline lens in the lens-bag 22 has been replaced by an optical element 12, a rangefinder that detects zonule tension or mechanical disturbances of the lens-bag 22 is a suitable choice. In patients having a loss of function in any of the foregoing anatomical structures, a rangefinder that incorporates an automatic focusing system similar to that used in an autofocus camera is a suitable choice.

Power Source

As noted above, the controller 16, the rangefinder 18, and the actuator 14 shown in FIG. 1 use a power source 20. In one embodiment, the power source 20 can be an implanted battery 68. The battery 68 can be implanted in any convenient location, such as under the conjunctiva 70 in the Therron's capsule, or within the sclera. Unless it is rechargeable in situ, such a power source 20 will periodically require replacement.

In another embodiment, the power source 20 can be a photovoltaic cell 72 implanted in a portion of the eye that receives sufficient light to power the vision prosthesis 10. The photovoltaic cell 72 can be mounted on a peripheral portion of the optical element 12 where it will receive adequate light without interfering excessively with vision. Alternatively, the photovoltaic cell can be implanted within the cornea 36, where it will receive considerably more light. When implanted into the cornea 36, the photovoltaic cell 72 can take the form of an annulus or a portion of an annulus centered at the center of the cornea 36. This configuration avoids excessive interference with the patient's vision while providing sufficient area for collection of light.

Power generated by such a photovoltaic cell 72 can also be used to recharge a battery 68, thereby enabling the vision prosthesis 10 to operate under low-light conditions. The use of a photovoltaic cell as a power source 20 eliminates the need for the patient to undergo the invasive procedure of replacing an implanted battery 68.

The choice of a power source 20 depends in part on the relative locations of the components that are to be supplied with power and the ease with which connections can be made to those components. When the optical element 12 is implanted in the cornea 36, for example, the associated electronics are likely to be accessible to a photovoltaic cell 72 also implanted in the cornea 36. In addition, a rechargeable subconjunctival battery 68 is also easily accessible to the photovoltaic cell 72. The disposition of one or more photovoltaic cells 72 in an annular region at the periphery of the cornea 36 maximizes the exposure of the photovoltaic cells 72 to ambient light.

When the optical element 12 is implanted in the anterior chamber 34, one or more photovoltaic cells 72 can be arranged in an annular region on the periphery of the optical element 12. This reduces interference with the patient's vision while providing sufficient area for exposure to ambient light. For an optical element 12 implanted in the anterior chamber 34, a rechargeable battery 68 implanted beneath the conjunctiva 70 continues to be conveniently located relative to the photovoltaic cells 72.

When the optical element 12 is implanted in the posterior chamber 24, one or more photovoltaic cells 72 can be arranged in an annular region of the optical element 12. However, in this case, the periphery of the optical element 12 is often shaded by the iris 26 as it contracts to narrow the pupil. Because of this, photovoltaic cells 72 disposed around the periphery of the optical element 12 may receive insufficient light to power the various other components of the vision prosthesis 10. As a result, it becomes preferable to dispose the photovoltaic cells 72 in an annular region having a radius small enough to ensure adequate lighting but large enough to avoid excessive interference with the patient's vision.

Modifications for Phakic Patients

In a patient who suffers from presbyopia (in the presence or absence of myopia, hyperopia, and/or astigmatism), correcting the eye for distance vision may not correct the eye for near vision. In such cases, one option is to remove the natural crystalline lens and to use an aphakic vision prosthesis as described above. An alternative is to avoid surgery to the natural crystalline lens and to instead use a phakic vision prosthesis.

The aphakic vision prosthesis and procedures described above can be used in a phakic vision prosthesis with some modifications. With a patient's natural crystalline lens intact, various portions of the optical element 12 may be positioned in any of a variety of locations (e.g., between the natural crystalline lens and the iris, in front of the iris, hooked to the iris, in the pupillary plane, in the cornea, or as a contact lens). Components such as the range-finder 18 should be positioned to measure electrical or mechanical stimuli without causing injury to the natural crystalline lens, zonules, or ciliary body.

In a phakic vision prosthesis it is desirable to compensate for any residual accommodation provided by the natural crystalline lens. This residual accommodation can cause changes in wavefront aberrations for different distances-of-regard. In addition, changes to the natural crystalline lens (e.g., in flexibility or gradient of index of refraction) may occur over time. These and other changes can be compensated for by changing wavefront data, in the case of embodiments having programmable wavefront correction, or by changing the shape of the ablated surface, in the case of embodiments that use a wavefront component 13.

It is to be understood that while the invention has been described in conjunction with the detailed description thereof, the foregoing description is intended to illustrate and not limit the scope of the invention, which is defined by the scope of the appended claims.

What is claimed is:

1. A method for reducing aberration in a human eye, the method comprising:
   receiving at a controller, from a rangefinder associated with the human eye, an estimated distance of an object-of-regard;
   accessing, by the controller, wavefront aberration data for the estimated distance based on predicted changes to optical path lengths in the eye that occur during an accommodation by the eye to focus on the object-of-regard;
   using the wavefront aberration data to generate wavefront data associated with refraction through an optical element disposed at a location in the eye; and
   providing by the controller to one or more actuators respective control signals that are based on the wavefront data, wherein each of the one or more actuators is configured to cause a change in a corresponding region of the optical element to provide a target characteristic function of the optical element, the target characteristic function being configured such that aberration in the eye is reduced.

2. The method of claim 1, further comprising storing the wavefront data in a memory element in electrical communication with the optical element.

3. The method of claim 1, wherein the wavefront aberration data is determined based on measurements obtained from anatomical features of the eye.

4. The method of claim 1, wherein the one or more actuators cause a change in an index of refraction profile of the optical element.

5. The method of claim 3, wherein the measurements are obtained while a patient is focusing on an object at a first distance and while the patient is focusing on an object at a second distance different from the first distance.

6. The method of claim 1, wherein the aberration is high-order aberration.

7. The method of claim 1, wherein the wavefront data is generated based on wavefront aberration data corresponding to a first predetermined position or orientation for the optical element within the eye.

8. The method of claim 7, wherein the wavefront data is generated based on wavefront aberration data corresponding to a second predetermined position or orientation for the optical element within the eye.

9. The method of claim 8, wherein the wavefront aberration data includes adjustments based on postoperative deviations in the second position or orientation of the optical element from the first predetermined position or orientation.

10. The method of claim 1, wherein the location in the eye is selected from the group consisting of:
    the anterior chamber;
    the posterior chamber;
    the lens-bag; and
    the cornea.

11. The method of claim 1, wherein the optical element is implanted in a phakic human patient.

12. The method of claim 1, wherein the optical element is implanted in an aphakic human patient.

13. The method of claim 6, wherein the high-order aberration comprises at least one of spherical aberration, coma, field curvature, and distortion.

14. The method of claim 1, wherein the rangefinder includes a transducer configured to detect a stimulus from a location within the eye.

15. The method of claim 14, wherein the location within the eye is one of a ciliary muscle, a zonule, or a lens-bag.

16. The method of claim 1, wherein the predicted changes are computed based on a theoretical model.

17. The method of claim 1, wherein the one or more actuators comprise an electrode that applies a field to change a refractive index in the corresponding region of the optical element.

18. The method of claim 1, wherein the one or more actuators comprise a mechanical actuator that deforms a reflecting or refracting surface associated with the corresponding region of the optical element.

19. The method of claim 1, wherein the one or more actuators comprise a contractile polymer based artificial muscle.

20. The method of claim 1, wherein the corresponding regions associated with the one or more actuators are distributed in a polar or rectilinear grid.

* * * * *